United States Patent [19]

Beyazov et al.

[11] Patent Number: 4,884,459
[45] Date of Patent: Dec. 5, 1989

[54] FLOW RATE CONVERTER

[75] Inventors: Yordan Y. Beyazov; Sasho G. Nenov; Vlayko S. Peychev, all of Sofia, Bulgaria

[73] Assignee: Institute Po Technicheska Kibernetika I Robotika, Sofia, Bulgaria

[21] Appl. No.: 208,188

[22] Filed: Jun. 16, 1988

[30] Foreign Application Priority Data

Jun. 16, 1987 [BG] Bulgaria ................................. 80178

[51] Int. Cl.⁴ ............................................... G01F 1/40
[52] U.S. Cl. ................................... 73/861.52; 73/202
[58] Field of Search .................. 73/198, 861.52, 202; 138/42, 44

[56] References Cited

U.S. PATENT DOCUMENTS 1,487,989  3/1924  Vose .................................. 73/861.52
3,220,256  11/1965  Weichbrod ......................... 73/861.52
4,418,723  12/1983  Koni et al. ......................... 73/861.52
4,434,976  3/1984  Murahami et al. .................... 138/42

Primary Examiner—Herbert Goldstein
Attorney, Agent, or Firm—Klein & Vibber

[57] ABSTRACT

A flow rate converter has a body with a cyclindric tube and an inlet and an outlet diffuser. The tube and body have inner annular conduits connecting with pipe connections disposed in the body. The body is also provided with a heating element. A replaceable cylindric body is inserted in the cylindric tube and is provided with first axial channels providing for a laminar flow and second axial channels of which at least one has a cross-sectional area at least two times larger than the cross-sectional area of the first channels. In both ends of the second channels are formed chambers while a replaceable cover with openings is fastened to the outlet diffuser.

5 Claims, 3 Drawing Sheets

FLOW RATE CONVERTER

FIELD OF THE INVENTION

The invention relates to a flow rate converter used in medical technology and in particular in the diagnosis of lung diseases.

BACKGROUND OF THE INVENTION

A known flow rate converter is disclosed in the catalog of the GOULD company (Netherlands). The known device has a body with a cylindric tube disposed therein. In the tube are disposed axial channels and its two ends are connected respectively with an incoming and an outgoing diffuser. In the body are machined inner circumferential conduits connecting the external row of axial channels with pipe connections disposed on the body to which is mounted a heating element. There are some several thousand axial channels which occupy the whole section of the tube and they have an approximately triangular section. In order to carry out investigations in the entire range, a series of ten converters with different parameters and overall sizes is needed.

The disadvantages of this known converter include complicated manufacture technology and the requirement of having an entire set of separate converters with different over-all sizes in order to cover the complete range.

SUMMARY OF THE INVENTION

An object of the invention is to provide a converter of flow rate with a simpler manufacture technology and be able to avoid the need of having an entire set of converters.

This object is attained by a flow rate converter comprising a body with a cylindric tube formed therein. In the tube, longitudinally axial channels are disposed and its two ends are connected respectively with an inlet and an outlet diffuser. In the body, a pair of inner annular conduits are machined connecting the external row of axial channels with pipe connections disposed on the body in which is mounted a heating element.

According to this invention, a replaceable cylindric body is disposed in the cylindric tube. On the circumferential surface of the cylindric body are formed first axial channels with a section providing for a laminar flow for which the Reynolds number is less than the critical. In the same cylindric body are disposed second axial channels of which at least one has cross-sectional area that is at least two times greater than the sum of the cross-sectional areas of the first axial channels and the flow in the second channels is turbulent.

Chamfers are formed in both ends of the second channels. For each replaceable cylindric body corresponds a replaceable cover with openings that is fastened to the outlet diffuser.

Advantages of this invention include simplified manufacture technology and the ability to use just one converter with replaceable cylindric bodies instead of a set of converters with different over-all sizes.

BRIEF DESCRIPTION OF THE DRAWING

With these and other objects in view, which will become apparent in the following detailed description, the present invention, which is shown by example only, will be clearly understood in connection with the accompanying drawing, in which.

DESCRIPTION OF THE PREFERRED EMBODIMENTS

Figure 1:
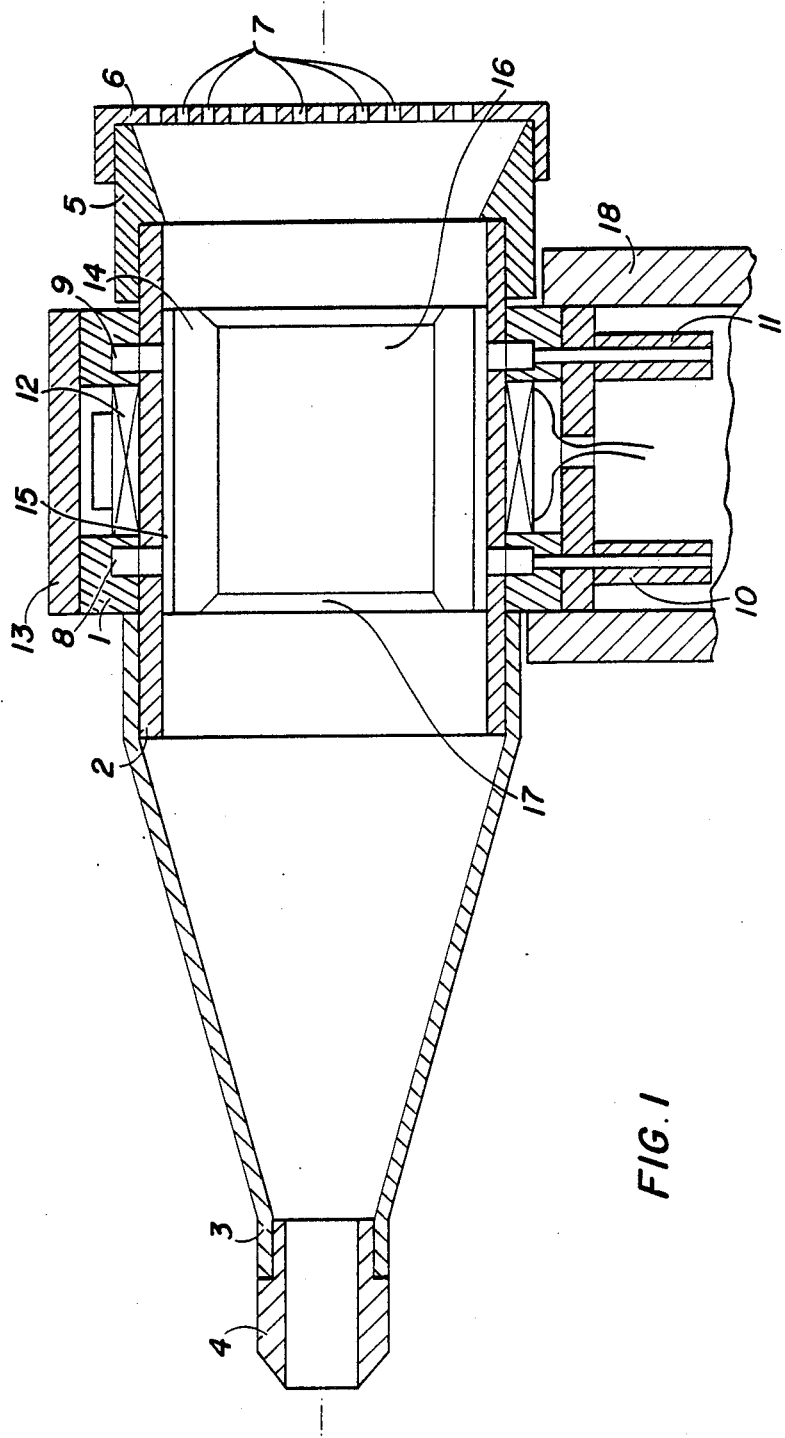
FIG. 1 is a longitudinal axial section of the flow rate converter.

The flow rate converter according to FIG. 1 comprises a body 1 in which is formed a cylindric tube 2 to the one end of which is fastened an inlet diffuser 3 with a nozzle 4. The other end of the tube 2 is fastened to an outlet diffuser 5 on which is placed a replaceable cover 6 with openings 7. Along the inner surface of the tube 2 have been machined two annular conduits 8 and 9 connected with two pipe connections respectively 10 and 11 which are disposed in the body 1. In the latter is inserted a heating element 12 closed by a cover 13.

Figure 3:
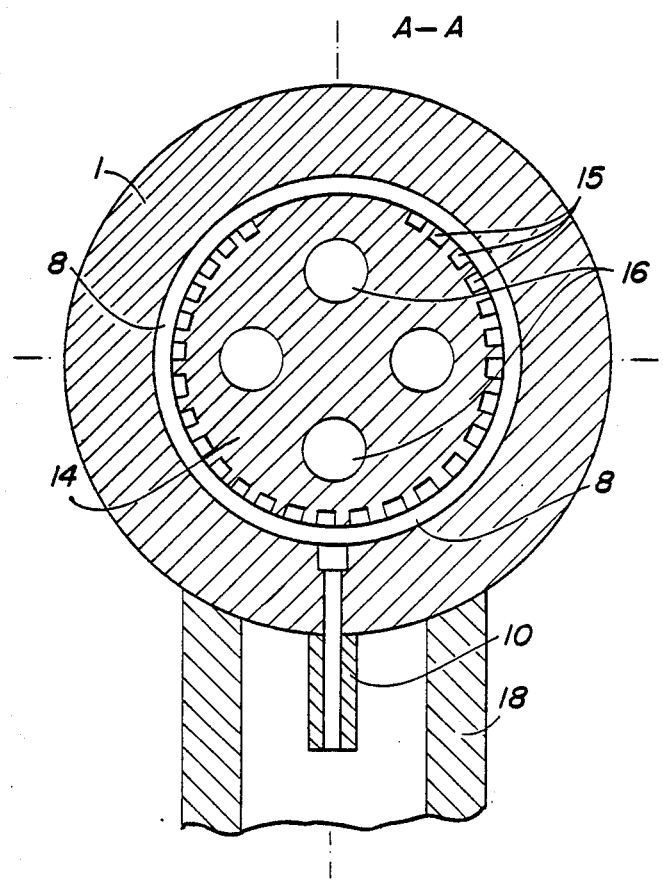
FIG. 3 is a section along A—A in FIG. 2.

A replaceable cylindric body 14 is mounted in the tube 2 and along the circumferential surface of the body 14 first axial channels 15 are formed (see also FIG. 3) with an equal rectangular cross-section. A second axial channel 16 is perforated in the replaceable body 14 and has a round cross-section having (in this embodiment) a cross-sectional area about 10 times larger than the sum of the cross-sectional areas of the first axial channels 15. In both ends of channel 16 are formed chamfers 17.

Figure 2:
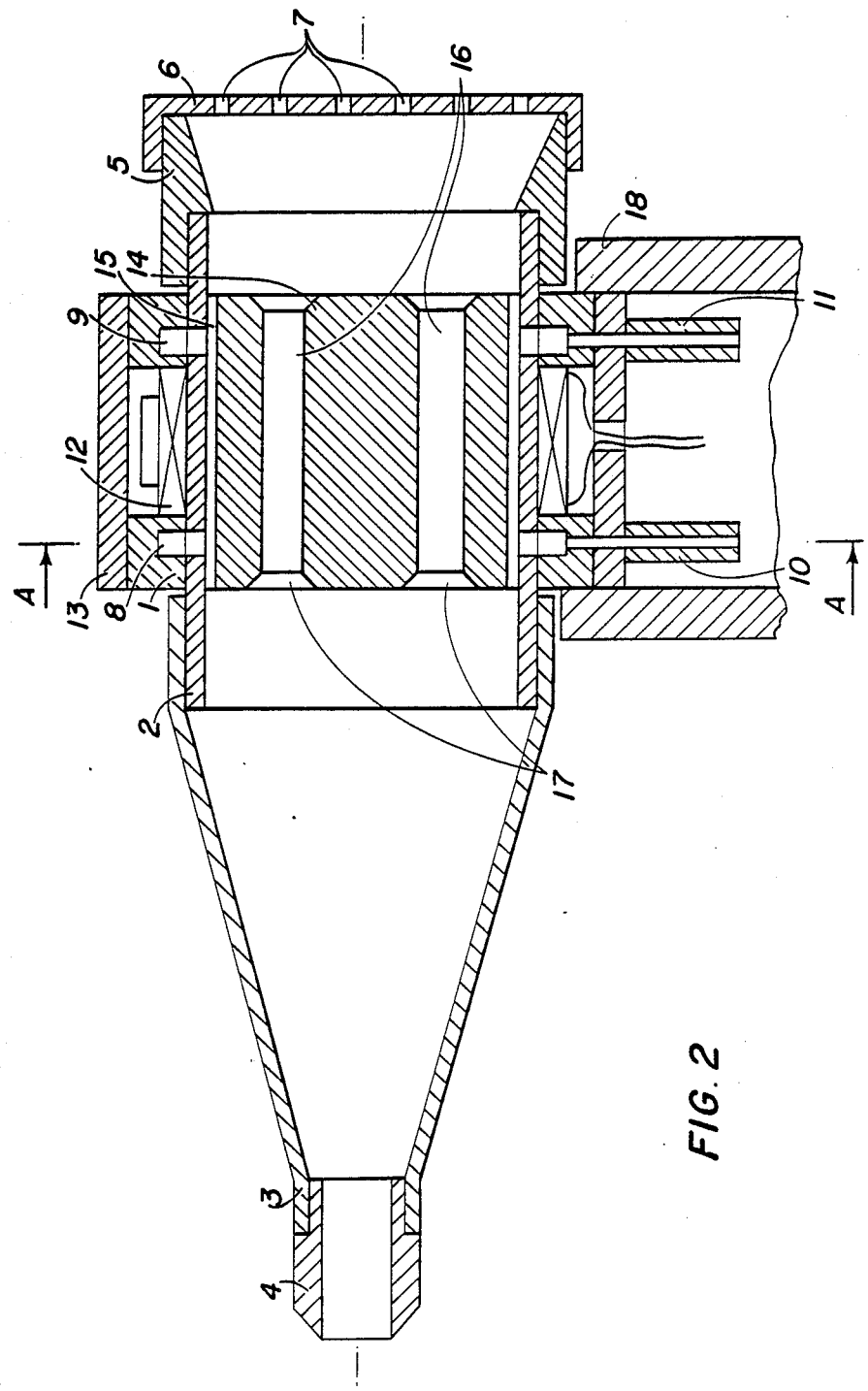
FIG. 2 is a view similar to FIG. 1 of variant of the flow rate converter.

The second axial channel 16 can have cylindric form or represent a combination of convergent and divergent parts with or without a cylindric part between them. A handle 18 may be fastened to the body 1. The body 1 and the tube 2 can represent and a single piece or can be separate pieces. The number of the first axial channels 15 ensuring a laminar flow should be the same for each replaceable cylindric body 14 whereas the number and diameter of the second axial channels 16 is specific for each cylindric body 14 depending on the required measuring range. Compare FIGS. 1, 2, and 3. In these channels the flow is turbulent.

The total cross-sectional area of the openings 7 on each replaceable cover 6 is equal to or less than the cross-sectional area of the second axial channels 16 of the respective replaceable cylindric body 14.

The pipe connections 10, 11 can be connected in series with a pneumoelectric converter of differential pressure, an electronic circuit for tuning, a microprocessor system for processing of the obtained results or a recording device (not shown in the figures) in order to obtain final results from the investigation.

The converter operates in the following manner:

The flow entering through the nozzle 4 and diffuser 3 is separated into two flows. The first flow is considerably smaller and passes through the first axial channels 15 which create a laminar flow whereas the second basic flow passes through the second axial channels 16 and is turbulent.

As a result of the laminar character of the flow through the first axial channels 15, the dependence between the generated pressure drop between the two pipe connections 10 and 11 and the flow rate is linear independently of the turbulent character of the flow through the second axial channels 16. The chamfers 17 augment considerably the flow rate coefficient. The replaceable cover 6 prevents any penetration of a backflow that would cause errors in measuring.

Although the invention is described and illustrated with reference to a plurality of embodiments thereof, it is to be expressly understood that it is in no way limited to the disclosure of such preferred embodiments but is capable of numerous modifications within the scope of the appended claims.

We claim:

1. A flow rate converter comprising
   a body with a cylindric tube formed therein;
   said tube being provided with inlet diffusing means at one end and outlet diffusing means at another end and a pair of spaced apart annular conduits;
   said body being provided with a heating element and two pipe means communicating with said two annular conduits;
   a replaceable cylindric body disposed in said tube, said replaceable body having a plurality of circumferential longitudinal axial channels communicating with said conduits;
   said cylindric body also having a non-circumferential axial channel;
   said non-circumferential channel having a cross-sectional area at least 2 times as large as the sum of the cross-sectional areas of said circumferential channels.

2. A flow rate converter as claimed in claim 1, further comprising
   said circumferential channels having a cross section providing for a laminar flow with a Reynolds number smaller than the critical.

3. A flow rate converter as claimed in claim 1, further comprising:
   said non-circumferential channel having chamfered ends.

4. A flow rate converter as claimed in claim 1, further comprising
   a replaceable cover, said cover being provided with openings and being fastened to the outlet diffuser.

5. A flow rate converter as claimed in claim 1, further comprising
   a plurality of non-circumferential channels.

* * * * *